United States Patent [19]

Asato

[11] 4,049,717

[45] Sept. 20, 1977

[54] NOVEL 1,2,3,4-TETRAHYDRO-4-OXO-(OXY)-1-NAPHTHYLAMINES AND METHOD OF PREPARATION THEREOF

[75] Inventor: Goro Asato, Titusville, N.J.

[73] Assignee: American Cyanamid Company, Stamford, Conn.

[21] Appl. No.: 685,945

[22] Filed: May 13, 1976

[51] Int. Cl.$^2$ .............. C07C 91/42; C07C 87/66
[52] U.S. Cl. .............. 260/575; 260/326 A; 260/326.5 C; 260/558 R; 260/558 P; 260/559 R; 260/559 S; 260/561 R; 260/561 HL; 260/578; 424/322; 424/324; 424/330
[58] Field of Search .................. 260/578, 575

[56] References Cited

U.S. PATENT DOCUMENTS

| | | | |
|---|---|---|---|
| 1,919,592 | 7/1933 | Klingemann et al. | 260/578 |
| 3,211,739 | 10/1965 | Schenker et al. | 260/558 R |
| 3,637,740 | 1/1972 | Sarges | 260/575 X |
| 3,704,323 | 11/1972 | Krapcho | 260/576 |
| 3,953,506 | 4/1976 | Spicer et al. | 260/553 A |
| 3,991,207 | 11/1976 | Sarges et al. | 260/575 X |
| 3,993,677 | 11/1976 | Asato | 260/453 AR |
| 4,003,930 | 1/1977 | Hauck et al. | 260/575 X |
| 4,005,140 | 1/1977 | Spicer et al. | 260/553 A |

OTHER PUBLICATIONS

Hassner et al., "JACS", vol. 90, pp. 2869-2875 (1968).

*Primary Examiner*—Daniel E. Wyman
*Assistant Examiner*—John J. Doll
*Attorney, Agent, or Firm*—Edward A. Conroy, Jr.

[57] ABSTRACT

This disclosure describes 1,2,3,4-tetrahydro-4-oxo-(oxy)-1-naphthylamine and novel derivatives thereof and methods of preparation of said compounds. These novel compounds are useful and valuable intermediates for the preparation of 1,2,3,4-tetrahydro-4-oxo(oxy)-1-naphthylurea and thiourea compounds and certain derivatives thereof which are animal growth promoters.

7 Claims, No Drawings

NOVEL 1,2,3,4-TETRAHYDRO-4-OXO-(OXY)-1-NAPHTHYLAMINES AND METHOD OF PREPARATION THEREOF

BACKGROUND OF THE INVENTION

The resolved 1,2,3,4-tetrahydro-1-naphthylamines have been reported in the literature by R. Weidmann and J. P. Guette, *Comptes Rendus des Seances de l'Academie des Sciences* 268:2225 (1969) as resulting from the Curtius reactions with optically active 1,2,3,4-tetrahydronaphthalene-1-carboxylic acid azides. This work establishes the absolute configuration of the (R) and (S) isomers, but does not suggest the 1,2,3,4-tetrahydro-4-oxo (oxy)-1-naphthylamines of the present invention, nor does it suggest the 1,2,3,4-tetrahydro-4-oxo (oxy)-1-naphthylureas or thioureas derived therefrom. The above urea and thiourea compounds are described and claimed in my application for United States Letters Patent Ser. No. 582,559, filed May 30, 1975, now abandoned.

Further, the above-referred-to article does not suggest the 1,2,3,4-tetrahydro-4-oxo (oxy)-1-naphthylisocyanates or isothiocyanates derived from the novel tetrahydro-4-oxo (oxy)-1-naphthylamines of the present invention. The above isocyanates and isothiocyanates are described and claimed in my application for United States Letters Patent Ser. No. 628,030, filed Nov. 3, 1975, now U.S. Pat. No. 3,993,677. Both applications are incorporated herein by way of reference.

This invention also relates to methods of preparation of the above-identified 1,2,3,4-tetrahydro-4-oxo (oxy)-1-naphthylamines.

BRIEF SUMMARY OF THE INVENTION

This invention relates to novel 1,2,3,4-tetrahydro-4-oxo (oxy)-1-naphthylamine compounds represented by formula (I) below:

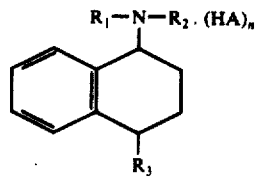

(I)

wherein $R_1$ is hydrogen; $R_2$ is selected from the group consisting of hydrogen, alkanoyl $C_1-C_7$, halogen-substituted alkanoyl

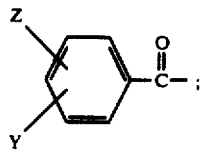

wherein Z and Y are each individually selected from the group consisting of hydrogen, halogen, nitro and alkoxy $C_1-C_4$; and when $R_1$ and $R_2$ are taken together with the associated nitrogen they represent a moiety selected from the group consisting of succinimido, maleimido and phthalimido; $R_3$ is oxo or the group— $OR_4$ wherein $R_4$ is hydrogen or alkyl $C_1-C_4$; HA represents an acid selected from HCl, HBr and HI; and $n$ is 0 except when $R_2$ is hydrogen. The term "halogen" refers to bromine, chlorine, fluorine and iodine.

A preferred group of compounds represented by formula (I) are those wherein $R_1$ is hydrogen, $R_2$ is selected from the group consisting of hydrogen, alkanoyl $C_1-C_7$, haloacetyl and benzoyl; and when $R_1$ and $R_2$ are taken together with the associated nitrogen they represent phthalimido; $R_3$ is selected from oxo and —$OR_4$ wherein $R_4$ is selected from hydrogen and alkyl $C_1-C_4$; and HA and $n$ are as defined above.

A more preferred group of compounds represented by formula (I) are those wherein $R_1$ is hydrogen; $R_2$ is selected from the group consisting of hydrogen, alkanoyl $C_1-C_7$ and benzoyl; and when $R_1$ and $R_2$ are taken together with the associated nitrogen they represent phthalimido; $R_3$ is selected from oxo, hydroxy and methoxy; and HA and $n$ are as defined above.

Another preferred group of compounds represented by formula (I) above are those wherein $R_1$ is hydrogen; $R_2$ is selected from hydrogen, formyl, acetyl, n-heptanoyl and benzoyl; and when $R_1$ and $R_2$ are taken together with the associated nitrogen they represent phthalimido; $R_3$ is selected from oxo, hydroxy and methoxy; and HA and $n$ are as defined above.

This invention relates to both the racemic mixtures and the optically active forms of the compounds identified by formula (I) above. The optically active isomers are designated as the (R) and (S) isomers, with the (S) isomers generally being preferred, since the tetrahydro-4-oxo(oxy)-1-naphthylureas and thioureas derived therefrom appear to be biologically more active than the (R) forms. The preferred (S) isomers may be illustrated as follows:

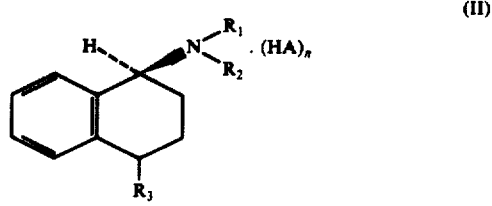

(II)

wherein $R_1$, $R_2$, $R_3$, HA and $n$ are as defined above. The (R) isomers corresponding to the above (S) isomers may be illustrated as follows:

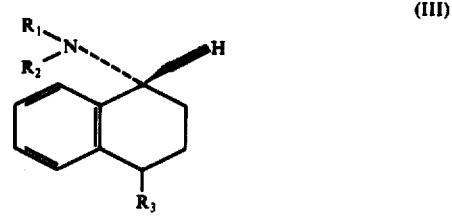

(III)

wherein $R_1$, $R_2$, $R_3$, HA and $n$ are as defined for said formula (II) (S) isomer. Hereinafter the terms (R) and (S) will refer to the absolute configuration at the 1 position of the molecule.

The above identified formulae (II) and (III) optically active tetrahydro-4-oxo(oxy)-1-naphthylamines have the same absolute configuration at the 1 position as the 1,2,3,4-tetrahydro-1-naphthylamine used as starting material. In order to obtain the formula (II) (S) isomer or the formula (III) (R) isomer, it is necessary to start with the corresponding (S) or (R) isomers of 1,2,3,4-tetrahydro-1-naphthylamine.

When $R_3$ is —$OR_4$, and $R_4$ is as defined above, the compounds obtained are the racemic mixtures, the cis and trans isomers, and the optical isomers thereof; wherein the terms cis and trans refer to the configuration of the —$OR_4$ group with respect to the 1-amino group.

It is recognized, of course, that the novel compounds of the present invention, as described and defined by formula (I) above, are representative of three distinct subclasses, dependent on the definition of $R_3$; i.e. the 4-oxo-, the 4-hydroxy- and the 4-alkoxy($C_1$-$C_4$)-tetrahydro-1-naphthylamines.

DETAILED DESCRIPTION OF THE INVENTION

In accordance with this invention, formula (I) 1,2,3,4-tetrahydro-4-oxo(oxy)-1-naphthylamines can be prepared as described and illustrated as follows.

A tetrahydro-1-naphthylamine compound of formula (Ia) is prepared by reacting the corresponding formula (IV) tetrahydro-1-naphthylamine with an oxidizing agent as graphically illustrated below:

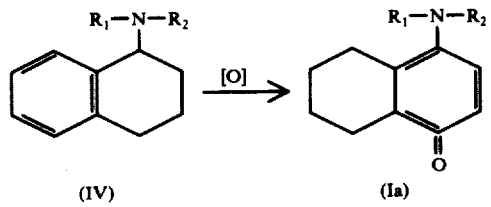

(IV)     (Ia)

wherein $R_1$ is hydrogen; $R_2$ is selected from alkanoyl $C_1$-$C_7$, halogen-substituted alkanoyl $C_1$-$C_7$ and

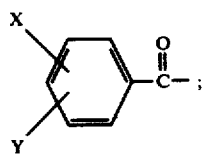

X and Y are selected from hydrogen, halogen, nitro and alkoxy $C_1$-$C_4$; and when $R_1$ and $R_2$ are taken together with the associated nitrogen they represent a moiety selected from the group of cyclic imides consisting of succinimido, maleimido and phthalimido; and said compounds are the racemic mixtures and the optical isomers thereof. While all oxidation reactions may not be effective, nevertheless the oxidation of a 1,2,3,4-tetrahydro-1-naphthylamine of formula (IV) to the corresponding tetrahydro-4-oxo-1-naphthylamine of formula (Ia) is novel and undisclosed.

Advantageously, one equivalent of a formula (IV) amine is reacted with 2 to 8 equivalents, and preferably with a 2 to 5 equivalents of an oxidizing agent selected from the group consisting of ceric ammonium nitrate, ceric sulfate, chromic anhydride, chromyl chloride, sodium bichromate, potassium persulfate/silver nitrate catalyst, silver oxide, potassium permanganate/ceric ammonium nitrate catalyst, hydrogen peroxide/vanadium pentoxide catalyst and t-butyl chromate at a temperature range of 0° C, and to 100° C., preferably 20° C. to 60° C., in a solvent selected from the group consisting of aqueous solutions of acetic acid, acetonitrile, tetrahydrofuran, dioxane, dimethoxyethane, diethylene glycol dimethyl ether, which may contain nitric acid, phosphoric acid or perchloric acid; or chromic anhydride — acetic anhydride, followed by hydrolysis.

Obviously, many other blocking groups not included in the above definition of $R_2$ can be used and that while some may give somewhat higher yields and/or easier workup, the net effect is the same in all cases, that is to protect the amino function during the oxidation step (for the conversion of formula (IV) compounds, to give compounds wherein $R_3$ is oxo).

Tetrahydro-1-naphthylamine compounds of formula (Ib), wherein said compounds are the racemic mixtures, the cis and trans isomers, and the optical isomers thereof, can be prepared by a reduction reaction from the corresponding formula (Ia) tetrahydro-4-oxo-1-naphthylamines as graphically illustrated below:

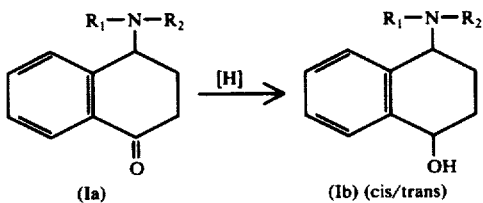

(Ia)     (Ib) (cis/trans)

wherein $R_1$ is hydrogen; $R_2$ is as defined above. While all reduction reactions may not be effective, nevertheless the reduction of a 1,2,3,4-tetrahydro-4-oxo-1-naphthylamine of formual (Ia) to the corresponding tetrahydro-4-hydroxy-1-naphthylamine of formula (Ib) (cis/trans) is novel and undisclosed.

Thus, formula (Ib) 1,2,3,4-tetrahydro-4-hydroxy-1-naphthylaines (cis/trans) are conveniently prepared from the corresponding formula (Ia) 4-oxo compounds by reduction with equimolar or excess amounts of sodium borohydride at a temperature range of 0° C. to 75° C., preferably 20° C. to 40° C., in $C_1$-$C_3$ alcohols, or alternatively with hydrogen in the presence of $PtO_2$ catalyst, at atmospheric to superatmospheric pressures of 15 to 100 psig, at a temperature range of 0° C. to 75° C., preferably 20° C. to 40° C., in $C_1$-$C_3$ alcohols, to afford a mixture of cis and trans isomers, as hereinabove defined.

Should formual (Ic) 1,2,3,4-tetrahydro-4-alkoxy $C_1$-$C_4$-1-naphthylamine compounds (cis/trans) be desired, these may be prepared by an alkylation reaction from the corresponding formula (Ib) tetrahydro-4-hydroxy-1-naphthylamines (cis/-trans), as graphically illustrated below:

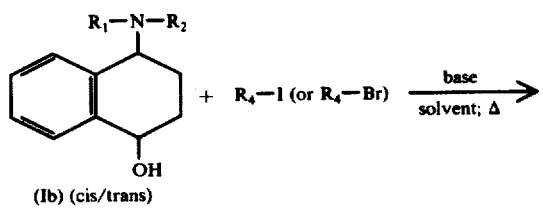

(Ib) (cis/trans)

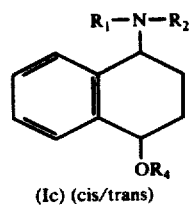

(Ic) (cis/trans)

wherein $R_1$ and $R_2$ are as defined above with the proviso that $R_2$ is not hydrogen and $R_4$ is alkyl $C_1$-$C_4$. While all alkylation reactions may not be effective, nevertheless the alkylation of a 1,2,3,4-tetrahydro-4-hydroxy-1-naphthylamine of formula (Ib) (cis/trans) to the corresponding tetrahydro-4-alkoxy-1-naphthylamine of formula (Ic) (cis/trans) is novel and undisclosed.

Thus, one equivalent of a formula (Ib) tetrahydro-4-hydroxy-1-naphthylamine (cis/trans) is reacted with 1 to 5 equivalents and preferably 1 to 3 equivalents of a $C_1$-$C_4$ alkyl halide (bromide, iodide) in an anhydrous solvent, inert to the reactants, such as tetrahydrofuran, dioxane, dimethoxyethane, diethylene glycol dimethyl ether, and the like, in the presence of a base such as sodium hydride or silver oxide, and the like, at a temperature range of 15° C. to 50° C., and preferably 20° C. to 30° C., for a period of time from about 1 hour to several days until the reaction is essentially complete, to afford a mixture of cis and trans isomers.

The 1,2,3,4-tetrahydro-1-naphthylamine intermediates of formula (IV), illustrated below:

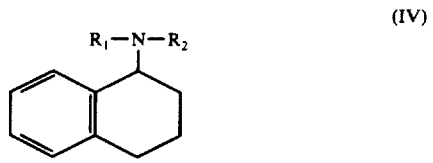

(IV)

wherein $R_1$ is hydrogen; $R_2$ is selected from the group consisting of alkanoyl $C_1$-$C_7$, halogen-substituted alkanoyl $C_1$-$C_7$ and

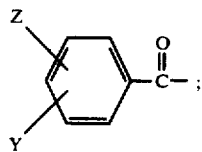

wherein Z and Y are selected from hydrogen, halogen, nitro and alkoxy $C_1$-$C_4$; and when $R_1$ and $R_2$ are taken together with the associated nitrogen they represent a moiety selected from the group of cyclic imides consisting of succinimido, maleimido and phthalimido; the racemic mixtures and the optical isomers thereof; are conveniently prepared from tetrahydro-1-naphthylamine by reacting one equivalent of said amine with a 1 to 1.5 equivalents of the appropriate acid anhydride or halide (preferably the acid chloride), in the presence of an anhydrous solvent, inert to the reactants, selected from aromatic hydrocarbons, such as benzene, toluene and xylene; chlorinated hydrocarbons, such as methylene chloride, chloroform, ethers, tetrahydrofuran, dioxane, dimethoxyethane, or mixtures thereof at a temperature range of 0° C. to 100° C., preferably 20° C. to 50° C., for a period of time of 1 to 24 hours. Acid acceptors, such as trimethyl or triethylamine, pyridine and the like, or alkali metal carbonates, such as sodium or potassium carbonate may be utilized to good advantage in the above reaction, especially when acid halides are employed.

The novel 1,2,3,4-tetrahydro-4-oxo(oxy)-1-naphthylamine compounds of formula (I) obtained by the procedures hereinabove described, are racemic mixtures. Should the optically active isomers of formula (I) compounds be desired, these may be conveniently prepared from the resolved, optically active isomers of 1,2,3,4-tetrahydro-1-naphthylamine by the above described routes.

The compounds of this invention represented and defined by formula (I) above, are useful and valuable intermediates for the preparation of animal growth promoting 1,2,3,4-tetrahydro-4-oxo(oxy)-1-naphthylurea and thiourea compounds. Preparation of said urea and thiourea compounds from the corresponding 1,2,3,4-tetrahydro-4-oxo(oxy)-1-naphthylamine compounds of the present invention represented by formula (I), may be accomplished by a number of alternate routes, a few of which are described and illustrated in detail in the following paragraphs.

A formual (I) amine wherein $R_3$ is oxo, except when $R_2$ is hydrogen, is hydrolyzed in dilute mineral acid or alkali, preferably acid (e.g. hydrochloric acid), while a formula (I) amine wherein $R_3$ is hydroxy or alkoxy $C_1$-$C_4$, except when $R_2$ is hydrogen, is hydrolyzed in dilute alkalie (e.g. potassium hydroxide), and the resulting formual (Id) amine is reacted with an equimolar or excess (5% to 50%) amount of sodium or potassium cyanate or thiocyanate at a temperature range of 0° C. to 100° C., preferably 0° C. to 70° C., in the presence of a solvent selected from the group consisting of water, $C_1$-$C_3$ alcohols, tetrahydrofuran, dioxane, ethylene glycol dimethyl ether, acetone, methyl ethyl ketone and the like, or mixtures thereof, in the pH range of 5 to 7, and preferably at pH 6, to yield the corresponding urea (or thiourea) of formula (V). The above reaction may be graphically illustrated as follows:

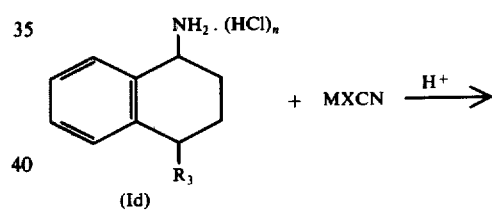

(Id)

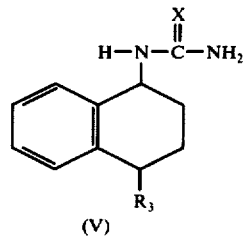

(V)

wherein $n$ is 0 or 1; $R_3$ is selected from oxo and $-OR_4$ and $R_4$ is alkyl $C_1$-$C_4$; X is oxygen or sulfur; M is sodium or potassium. The formula (V) ureas and thioureas obtained are the racemic mixtures and the cis and trans isomers thereof when $R_3$ is alkoxy $C_1$-$C_4$. Reduction of the above formula (V) oxo compounds with sodium borohydride or with $H_2$/$PtO_2$ as hereinbefore described, yields the corresponding 4-hydroxy (cis/-trans) analogs.

To obtain a formula (V) substituted urea (or thiourea), a formula (Id) amine (wherein n is O or l) is reacted with an isocyanate or isothiocyanate of formula: $R_5$-NCX under conditions similar to those described above, to yield a formula (V) urea of the structure:

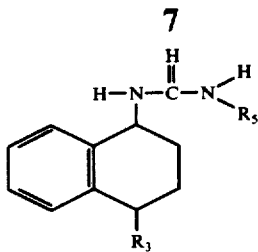

wherein R₃ is selected from oxo and —OR₄ and R₄ is hydrogen or alkyl C₁-C₄; X is oxygen or sulfur; R₅ represents a substituent such as alkyl, alkoxy, benzyl, phenyl, substituted phenyl and the like, to enhance the biological activities and or impart suitable physical properties to said ureas. The formula (V) substituted ureas and thioureas obtained are the racemic mixtures and the cis and trans isomers thereof when R₃ is hydroxy or alkoxy C₁-C₄. When in the above reaction a formula (Id) amine acid salt (i.e. n is 1) is employed, an acid acceptor, such as a trialkylamine (e.g. triethylamine), pyridine and the like, may be utilized to good advantage in said reaction. Reduction of the above formula (V) oxo compounds with sodium borohydride or with H₂/PtO₂ as hereinbefore described, yields the corresponding 4-hydroxy (cis/trans) analogs.

Alternatively, an amine of formula (Id), wherein n is 0 or 1; R₃ is oxo or alkoxy C₁-C₄, is reacted with phosgene, preferably under anhydrous conditions and under a blanket of inert gas such as nitrogen. The reaction is initially carried out at a temperature range of 0° C. to 40° C., preferably 10° C. to 20° C., and then heated to between 50° C. and about 100° C., preferably from 60° C. to 80° C. to yield an isocyanate of formula (VI):

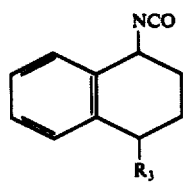

(VI)

wherein R₃ is oxo or —OR₄ and R₄ is alkyl C₁-C₄. This reaction is usually conducted in the presence of a solvent such as benzene, toluene or xylene. The thus obtained isocyanate of formula (VI) is then reacted with an equimolar or excess (5% to 50%) amount of an amine of formula:

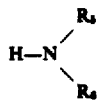

to yield a formula (V) urea of the structure:

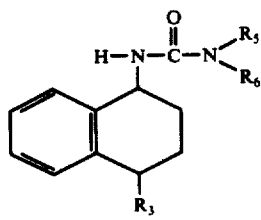

(V)

wherein R₃ is oxo or alkoxy C₁-C₄; R₅ and R₆ represent substitutents such as alkyl, alkoxy, benzyl, aryl groups and the like, selected to enhance the biological activity and/or physical properties of said urea. The thus obtained ureas of formula (V) are the racemic mixtures and the cis and trans isomers thereof when R₃ is alkoxy C₁-C₄. Reduction of the above ureas, when R₃ is oxo, with sodium borohydride or with H₂/PtO₂ yields of the corresponding 4-hydroxy (cis/trans) analogs.

The analogous thioureas of formula (V) can be prepared by reacting a formula (Id) (wherein n is 0) amine with equimolar amounts of carbon disulfide, triethylamine and a carbodiimide represented by the formula: G—N=C=N—G, where G is cyclohexyl, cycloheptyl, alkyl C₄-C₆ and the like. This reaction is generally conducted in the presence of a solvent such as tetrahydrofuran or diethyl ether, at a temperature between −10° C. and +25° C. The product can be isolated by distillation or by dry-column chromatography. The thus obtained isothiocyanates are then reacted with ammonia or with an amine of formula:

$$H-N\begin{matrix}R_5\\R_6\end{matrix}$$

to yield a formula (V) thiourea of the structure:

(V)

wherein R₃, R₅ and R₆ are as defined above, and said thioureas are the racemic mixtures and the cis and trans isomers thereof when R₃ is alkoxy C₁-C₄. The above reaction sequence may be graphically illustrated as follows:

wherein R₃, R₅, R₆ and G are as defined above. Reduction of the above formula (V) oxo-thioureas with sodium borohydride as hereinbefore described, yields the corresponding 4-hydroxy (cis/trans) analogs.

Similarly, an amine of formula (Id), wherein n is 0 or 1; R₃ is oxo or —OR₄ and R₄ is alkyl C₁-C₄, is reacted with an appropriately substituted carbamic or thiocarbamic acid chloride (or bromide) of formula:

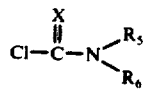

to yield a formula (V) urea (thiourea) of the structure:

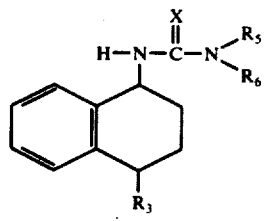

wherein $R_3$ is as defined above; X is oxygen or sulfur; $R_5$ and $R_6$ represent substitutents such as alkyl, alkoxy, benzyl, aryl groups and the like, selected to enhance the biological activity and/or physical properties of said ureas. The formula (V) ureas (thioureas) thus obtained are the racemic mixtures and the cis and trans isomers thereof when $R_3$ is alkoxy $C_1$-$C_4$.

Advantageously this reaction is carried out in the presence of an aromatic solvent, such as benzene, toluene and xylene, a halogenated hydrocarbon, such as methylene chloride, chloroform and dichloroethane, ketones, such as acetone, methyl ethyl ketone, ethers, such as tetrahydrofuran, dimethoxyethane and the like, or mixtures of said solvents. The reaction can be conducted at a temperature range of 0° C. to 100° C., preferably 0° C. to 70° C. In the above reaction, it is desirable to add an acid acceptor to the reaction mixture. Suitable acid acceptors include trialkylamines such as triethylamine, trimethylamine and the like, pyridine, alkali metal carbonates such as sodium or potassium carbonate, and the like.

Reduction of the above formula (V) oxo-ureas (and thioureas) with sodium borohydride or with $H_2$/$PtO_2$ as hereinbefore described, yields the corresponding 4-hydroxy (cis/-trans) analogs.

The animal-growth-promoting urea and thiourea compounds of formula (V), prepared from the novel compounds of the present invention, are the racemic mixtures and the cis and trans isomers thereof when $R_3$ is hydroxy or alkoxy $C_1$-$C_4$; unless, of course, the reaction sequence leading to said ureas (and thioureas) is started with the resolved amines of formula (I).

The 1,2,3,4-tetrahydro-4-oxo(oxy)-1-naphthylurea (and thiourea) compounds of formula (V) are useful as growth promoting agents for poultry such as chickens, ducks, geese, guinea hens and the like; fur-bearing animals such as rabbits, foxes, chinchillas, minks and the like; farm animals, such as cattle, sheep, goats, swine and the like. The use of said compounds for this purpose has the added advantage of improveing feed conversion for said animals. The term "feed conversion" means the ratio of unit weight of feed per unit weight of gain and "improvement in feed conversion" means increased weight gain from a given unit of feed consumed.

A growth-promoting amount of a formula (V) 1,2,3,4-tetrahydro-4-oxo(oxy)-1-naphthylurea (thiourea) or an optically active isomer thereof is administered to a host animal in, or with, the animal's feed. Said compound may also be administered as a subcutaneous implant under the skin of said animal or as a parenteral injection.

When administered in the feed of said animals, usually about 0.0001% to about 0.08% by weight, and preferably 0.001% to 0.04% by weight of formula (V) urea, is effective for increasing growth rate and improving feed conversion. When administered as a parenteral injection or subcutaneous implant, usually in amounts that will supply about 0.0005 mg. to about 0.2 mg, preferably 0.001 mg to 0.10 mg per kg of body weight per day of the active compound, it will produce the desired improvement in weight gain and enhance feed conversion.

The present invention is further illustrated by the specific examples set forth below.

EXAMPLE 1

Preparation of N-(1,2,3,4-tetrahydro-4-oxo-1-naphthyl)formamide

A solution of 31.4 g. of chromic anhydride in 140 ml. of acetic anhydride is added dropwise over 80 minutes to a stirred solution of 20 g. of N-(1,2,3,4-tetrahydro-1-naphthyl)formamide in 120 ml. of acetic anhydride, while maintaining the temperature of the reaction mixture between −8° C. to 4° C. The reaction mixture is then stirred an additional 35 minutes at 3° C., poured into an ice-water mixture and stirred overnight. The mixture is filtered and 1.5 g. of solid collected. The filtrate is saturated with sodium chloride and extracted with 2 × 1000 ml. of methylene chloride. The combined organic extracts are washed with 1000 ml. of brine and evaporated to dryness in vacuo. The oily residue is triturated with 200 ml. of ether to afford a tan solid, the mixture stirred for a while and is then filtered. The collected tan solid is washed with 2 × 5 ml. of ether to afford 13 g. of product, melting point 103°-106° C.

Substitution of sodium or potassium bichromate in the above reaction also affords the title compound.

The title compound is also prepared by reacting N-(1,2,3,4-tetrahydro-1-naphthyl)formamide with four equivalents of ceric sulfate or ceric ammonium nitrate is 50% aqueous acid at room temperature for 10 minutes. The reaction mixture is then filtered, poured into water and extracted with chloroform. The chloroform extract is evaporated to dryness in vacuo to afford the title compound.

Similarly, (+)- and (−)-N-(1,2,3,4-tetrahydro-1-naphthyl) formamides are oxidized by the above procedures to afford (+)- and (−)-N-(1,2,3,4-tetrahydro-4-oxo-1-naphthyl) formamides.

EXAMPLE 2

Preparation of 1,2,3,4-Tetrahydro-4-oxo-1-naphthylamine hydrochloride

A solution of 19.6 g. of N-(1,2,3,4-tetrahydro-4-oxo-1-naphthyl) formamide in 214 ml. of 95% ethanol and 214 ml. of 2N hydrochloric acid is heated at reflux for 3 hours and then stirred at room temperature for 2 days. The solution is filtered and the filtrate concentrated in vacuo to afford a dark residue. The residue is dried by adding ethanol and evaporating the mixture in vacuo. This procedure affords 20.2 of the title compound, melting point 200°-216° C. (dec.).

EXAMPLE 3

Preparation of 1,2,3,4-Tetrahydro-4-oxo-1-naphthylurea

A solution of 11.0 g. of N-(1,2,3,4-tetrahydro-4-oxo-1-naphthyl) formamide in 120 ml. of 95% ethanol and 120 ml. of 2N hydrochloric acid is heated at reflux for 3 hours and then stirred at room temperature overnight. The solution is filtered and concentrated in vacuo to afford a brownish-red solid. About 120 ml. of ethanol is added to the solid and the mixture is then further concentrated in vacuo to yield 11.3 g. of solid. This solid is added to 60 ml. of water and filtered. The insoluble residue is washed with 16 ml. of water and the aqueous fractions are combined, stirred and a solution of potassium cyanate in 24 ml. of water added dropwise. The mixture is stirred overnight, the precipitated brown solid collected and washed with water and then with cold methanol to afford 10.4 g. of the title compound, a grayish-brown solid, melting point 235°–238° C. (dec.).

EXAMPLE 4

Preparation of 1,2,3,4-Tetrahydro-4-hydroxy-1-naphthylurea (cis and trans isomeric mixture)

To a stirred solution of 4.6 g. of 1,2,3,4-tetrahydro-4-oxo-1-naphthylurea in 230 ml. of ethanol 0.85 g. of sodium borohydride is added. The reaction mixture is stirred for about 5 hours and after standing overnight 50 ml. water is added while stirring. The mixture is then evaporated in vacuo to remove the solvent. Water (50 ml.) is added, then glacial acetic acid is added, until the foaming caused by the acid ceases. The solution is evaporated to dryness in vacuo, alcohol is added and the whole evaporated to dryness in vacuo. Then 30 ml. of ethanol is added to the residue and the mixture stirred and filtered. The collected insoluble solid is air dried. This solid is heated with 300 ml. of acetone and filtered. The filtrate is concentrated in vacuo to afford 0.55 g. of the title compound, melting point 170°– 176° C. On further work-up of the acetone mother liquor, 0.2 g. of the title compound, melting point 169°–174° C., is recovered.

The original ethanol filtrate is evaporated to dryness in vacuo and the residue dissolved in 300 ml. of hot acetone. The acetone solution is filtered and concentrated to afford white crystals, which are collected and washed with cold acetone to afford an additional 1.4 g. of title compound, melting point 175°–177° C.

EXAMPLE 5

Preparation of 1-Methyl-3-(1,2,3,4-tetrahydro-4-oxo-1-naphthylurea

To a stirred mixture of 10 g. of 1,2,3,4-tetrahydro-4-oxo-1-naphthylamine hydrochloride in 200 ml. of dry tetrahydrofuran (THF) under a nitrogen atmosphere, 76 ml. of triethylamine is added dropwise. The mixture is stirred for an additional 5 minutes, and 3 ml. of methylisocyanate is added dropwise. The reaction mixture is stirred 1 hour at room temperature and the solid collected. The filter cake is washed with THF and then with 3 × 50 ml. of water. The THF filtrate is concentrated in vacuo to afford some product. The water-insoluble solid is air dried to afford 8.8 g. of the title compound, melting point 219°–221° C. Recrystallization from about 150 ml. of methanol yields 7.4 g. of the above product, melting point 220°–223° C.

EXAMPLE 6

Preparation of 1-Methyl-3-(1,2,3,4-tetrahydro-4-hydroxy-1-naphthyl) urea (cis and trans isomeric mixture)

1-Methyl-3-(1,2,3,4-tetrahydro-4-oxo-1-naphthyl)-urea (3.3 g.) is hydrogenated in the presence of 0.3 g. of $PtO_2$ 0.05 mmole $FeCl_3$ solution in 300 ml. of 95% ethanol using a low-pressure all-glass hydrogenator. After 615 ml. of hydrogen is absorbed, the excess hydrogen is removed by purging the system with nitrogen. The solution is filtered and evaporated to dryness in vacuo to afford 3.4 g. of an oil. The oil is stirred with about 20 ml. of acetone and the formed white solid is collected to afford 1.6 g. of the title compound as a cis/trans mixture, melting point 172°–180° C.

EXAMPLE 7

Preparation of (+)- and (−)-1,2,3,4-Tetrahydro-4-oxo-1-naphthylurea

By the method of Example 3, (+)- and (−)-N-(1,2,3,4-tetrahydro-4-oxo-1-naphthyl) formamide are hydrolyzed and reacted with sodium or potassium cyanate to afford (+)- and (−)-1,2,3,4-tetrahydro-4-oxo-1-naphthylurea, respectively.

EXAMPLE 8

Preparation of N-(1,2,3,4-tetrahydro-4-oxo-1-naphthyl)acetamide 1,2,3,4-Tetrahydro-1-naphthylaine is stirred with acetic anhydride to afford N-(1,2,3,4-tetrahydro-1-naphthyl) acetamide, which is oxidized to N-(1,2,3,4-tetrahydro-4-oxo-1-naphthyl) acetamide by the method of Example 1.

Similarly, oxidation of N-(1,2,3,4-tetrahydro-1-naphthyl) acetamide with ceric ammonium nitrate, $K_2S_2O_8$/catalytic $AgNO_3$, $KMnO_4$/catalytic ceric ammonium nitrate, t-butyl chromate, $Na_2Cr_2O_7$, ceric sulfate, chromyl chloride and $H_2O_2/V_2O_5$, respectively, under standard conditions and the general workup conditions described in Example 1, also affords the title compound.

EXAMPLE 9

Preparation of cis and trans-N-(1,2,3,4-tetrahydro-4-hydroxy-1-naphthyl) acetamide A mixture of 19.2 g. of N-(1,2,3,4-tetrahydro-4-oxo-1-naphthyl) acetamide and 275 ml. of absolute ethanol is stirred under a nitrogen atmosphere and 3.58 g. sodium borohydride added. The reaction mixture is stirred at room temperature for 16 hours, then 200 ml. of water is added and the stirring continued for 4 hours. Next, the reaction mixture is evaporated to dryness in vacuo and the residue treated with 250 ml. of water. The mixture is cooled in an ice bath and acidified with concentrated hydrochloric acid. The precipitated yellow solid is collected and dried; weight 6 g., m.p. 120°–127° C.

The aqueous filtrate is extracted with chloroform (2 × 50 ml.), the chloroform extract is dried and evaporated to dryness to afford 3 g. of resinous material. On standing, the aqueous mother liquor deposits white crystals which are collected and dried; weight 4 g., m.p. 163°–173° C. This crystalline material is recrystallized twice from acetone to give the title compound, m.p. 179°-181° C.

By liquid-liquid extraction (CHCl₃) of the aqueous mother liquor an additional 6.1 g. of material is obtained. This material is recrystalized from acetone to yield additional title compound.

EXAMPLE 10

Preparation of cis and trans-N-(1,2,3,4-tetrahydro-4-methoxy-1-naphthyl)acetamide A mixture of cis and trans-N-(1,2,3,4-tetrahydro-7-hydroxy-1-naphthyl) acetamide (3.9 g.) and 150 ml. tetrahydrofuran (THF) is stirred and 17 ml. of methyl iodide and 24.4 g. of freshly prepared silver oxide are added over a 4 hour period, under a nitrogen atmosphere. After 16 hours, an additional 10 ml. of methyl iodide and 11.4 g. of silver oxide are added over a 4 hour period and stirring is continued for 2 days. The mixture is filtered through a layer of celite and the filter cake washed with THF (2× 75 ml.). The filtrate and wash solution are combined and evaporated to dryness in vacuo to afford 4.3 g. of solid. The solid is recrystallized from hexane/ether to afford 2.4 g. of title compound, m.p. 97°-100° C.

Similarly, substituting ethyl iodide, n-propyl iodide, isopropyl iodide and n-butyl iodide for methyl iodide in the above preparation affords the corresponding 4-ethoxy, 4-n-propoxy, 4-isopropoxy and 4-n-butoxy derivatives, respectively.

EXAMPLE 11

Preparation of cis and trans-1,2,3,4-tetrahydro-4-methoxy-1-naphthylamine

A mixture of 6.9 g. of cis and trans-N-(1,2,3,4-tetrahydro-7-methoxy-1-naphthyl) acetamide, 56.11 g. of potassium hydroxide, 50 ml. of ethylene glycol and 20 ml. of water is stirred and heated at reflux for a overnight period. The mixture is cooled, 100 ml. of water is added and the mixture extracted with methylene chloride (3×50 ml.). The combined extracts are washed with 125 ml. of 10% sodium hydroxide solution, dried and evaporated in vacuo to afford 5.7 g. of title product as an oil. This oily amine is used without further purification for the preparation of the urea derivative.

Hydrolysis of the 4-ethoxy, 4-n-propoxy, 4-isoproposy and 4-n-butoxy homologs in the same manner affords the corresponding naphthylamines.

EXAMPLE 12

Preparation of cis and trans-1,2,3,4-tetrahydro-4-methoxyl1-naphthylurea

A 5.4 g. sample of cis/trans-1,2,3,4-tetrahydro-7-methoxy-1-naphthylamine and 20 ml. of water are mixed, stirred and the pH of the mixture adjusted to 6 with 4N hydrochloric acid. The resulting solution is filtered through glass wool, 6.15 g. potassium cyanate is added and the reaction mixture stirred overnight. The white precipitate formed is collected, washed with water and dried to afford 5.7 g. of the title compound, m.p. 159°-165° C. Recrystallization from ethyl acetate affords 3.8 g., m.p. 173°-177° C.

EXAMPLE 13

Preparation of N-(1,2,3,4-tetrahydro-4-oxo-1-naphthyl)acetamide

By the procedure of Example 1, N-(1,2,3,4-tetrahydro-1-naphthyl) acetamide is oxidized with chromic anhydride to afford the title compound, m.p. 128°-130° C. after recrystallization from ethyl acetate.

EXAMPLE 14

Preparation of 1,2,3,4-Tetrahydro-4-oxo-1-naphthylamine

A mixture of 41.4 g. of crude N-(1,2,3,4-tetrahydro-4-oxo-1-naphthyl) acetamide, 300 ml. of concentrated hydrochloric acid and 250 ml. of water is stirred and heated at reflux overnight. The mixture is decanted, filtered, and the cooled filtrate is extracted with 300 ml. of chloroform. The aqueous solution is evaporated to dryness in vacuo to afford 26.55 g. of the title product.

EXAMPLE 15

Preparation of 1,2,3,4-tetrahydro-4-oxo-1-naphthylurea

A sample of 26.55 g. of 1,2,3,4-tetrahydro-4-oxo-1-naphthylamine hydrochloride is dissolved in 250 ml. water and a solution of 21.8 g. of potassium cyanate in 75 ml. of water added. The reaction mixture is stirred for 72 hours, the precipitate formed in the reaction is collected by filtration and dried to afford 21.45 g. of the title compound, m.p. 225° C. (dec.).

EXAMPLE 16

Preparation of 4-oxo-1,2,3,4-tetrahydro-1-naphthylamides

By the procedure of Example 1, 1,2,3,4-tetrahydro-1-naphthylamides are oxidized to the corresponding 4-oxo derivatives. The amides are prepared by conventional acylation methods (acid chlorides or anhydrides).

The amides and the oxo compounds derived therefrom are shown in the tabulation appended thereto.

Table I $$\text{A} \xrightarrow{[O]} \text{B}$$

where A is the R₁—N—R₂ substituted tetrahydronaphthyl and B is the corresponding 4-oxo derivative.

| R₁ | R₂ | m.p. ° C. of A | m.p. ° C. of B |
|---|---|---|---|
| H | n-C₆H₁₃—C(O)— | 69–73 | Identified by infrared, used directly in Example 17 |
| H | C₆H₅—C(O)— | 113–117 | " |
| | phthaloyl (O=C—C₆H₄—C=O) | 123–129 | 143–157 |

In the same manner, the following 4-oxo-1,2,3,4-tetrahydro-1-naphthylamides are prepared wherein R₂ is defined as:

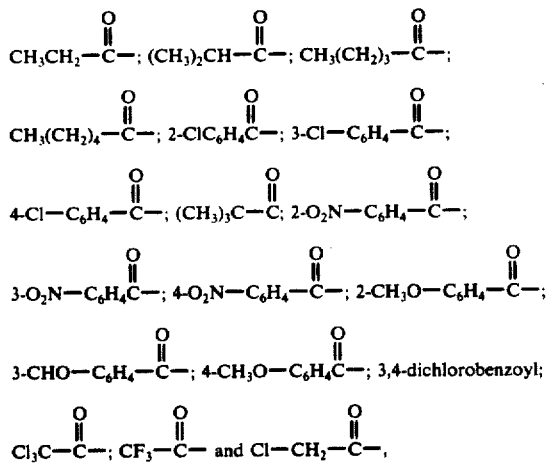

and when $R_1$ and $R_2$ are taken together with the associated nitrogen they represent succinimido and maleimido. The starting materials (A) are prepared by reacting the corresponding acid anhydrides or acid chlorides with 1,2,3,4-tetrahydro-1-naphthylamine in an inert solvent such as benzene. When an acid chloride is used, an equivalent of triethylamine is added to the reaction mixture.

EXAMPLE 17

Preparation of 1,2,3,4-Tetrahydro-7-oxo-1-naphthylurea

By the procedures of Examples 14 and 15, the following compounds are converted to the title compound, identified by infrared and nuclear magnetic resonance spectroscopy.

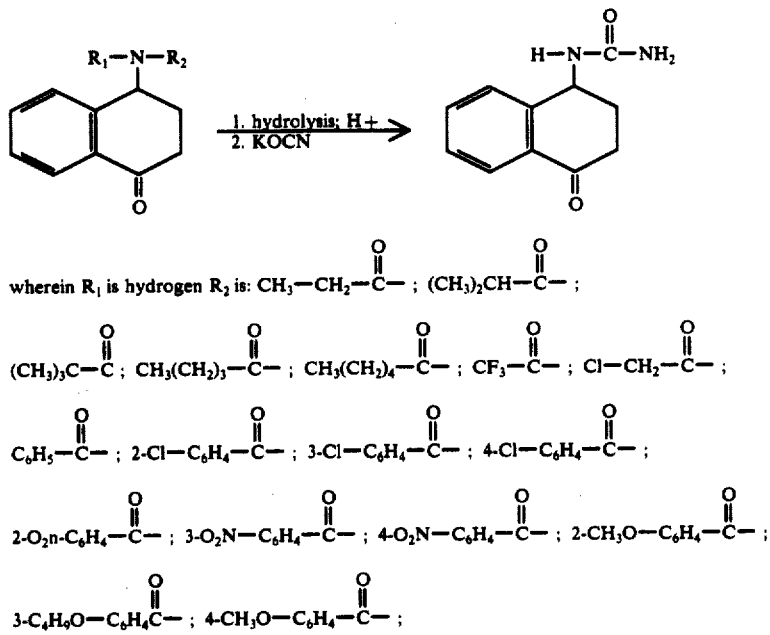

3,4-dichlorobenzoyl, and when $R_1$ and $R_2$ are taken together with the associated nitrogen they represent succinimido and phthalimido.

EXAMPLE 18

Preparation of 1,2,3,4-Tetrahydro-4-oxo-1-naphthyl isothiocyanate

A solution of 1,2,3,4-tetrahydro-4-oxo-1-naphthylamine (1.74 g.) in ethyl acetate (25 ml.) is stirred under a nitrogen atmosphere and triethylamine (1.37 ml.) is added. The solution is cooled in an ice-bath for 15 minutes and carbon disulfide (0.66 ml.) added. A white precipitate forms. The mixture is stirred for 15 minutes at 5° C. to 10° C. and a solution of dicyclohexylcarbodiimide (2.1 g.) in ethyl acetate (25 ml.) is added dropwise. After stirring overnight, the reaction mixture is filtered and the filtrate evaporated to dryness in vacuo to afford the title isothiocyanate, which has an infrared absorption maximum at 20755 cm$^{-1}$.

EXAMPLE 19

Preparation of 1-Ethyl-3-(1,2,3,4-tetrahydro-4-oxo-1-naphthyl)-2-thiourea

To a solution of 1,2,3,4-tetrahydro-4-oxo-1-naphthyl isothiocyanate (5.0 g.) in methylene chkloride (100 ml.), ethylamine is added via ethanol )15 ml.) saturated with ethylamine. After stirring for 18 hours, the mixture is heated at reflux for 2 hours, cooled and evaporated to dryness in vacuo. The residue is triturated with water and the title compound collected and drid; m.p. 134° C. to 138° C.

Similarly, treatment of the isothiocyanate with alcoholic or aqueous solutions of methylamine and dimethylamine afford 1-methyl- and 1,1-dimethyl-3-(1,2,3,4tetrahydro-4-oxo-1-naphthyl)-2-thiourea, respectively.

EXAMPLE 20

Mouse Growth Regulant Tests

CFI female mice from Carworth Farm are received when they are 6 weeks old. They are housed 10 to a cage in air-conditioned rooms (72° F. to 76> F.) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of 10 and assigned at random to the different treatments. The concentration of the different compounds in the diet is indicated in the following Table. Twelve days later the mice are weighed again and the experiment terminated. At least 3 cages (30 mice) of untreated controls are included in each test. Test data are provided in Table II below wherein data are reported as percent weight gain over controls. The following is a description of the diet to which the growth promoting compounds are added.

| Diet | |
|---|---|
| Guaranteed Analysis | |
| Crude Protein not less than | 23.0% |
| Crude fat not less than | 4.5% |
| Crude fiber not more than | 6.0% |
| Ash not more than | 9.0% |
| Ingredients | |
| Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide. | |

Table II

Effectiveness of 1,2,3,4-Tetrahydro-4-oxo(oxy)-1-naphthylureas (and thioureas) as Animal Growth Promoting Agents Reported as Percent Weight Gain Over Controls Using Mice as the Test Animal

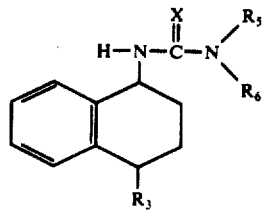

| Rate ppm in Diet | $R_3$ | $R_5$ | $R_6$ | X | % Weight Gain Over Controls |
|---|---|---|---|---|---|
| 50 | | H | H | O | 35.71 |
| 100 | ‖ O | | | | 97.40 |
| 200 | | | | | 93.51 |
| 200 | ‖ O | $CH_3$ | H | O | 69.00 |
| 400 | ‖ O | 2-$C_4H_9$ | H | O | 19.00 |
| 400 | \| OH cis/trans | H | H | O | 95.00 |
| 200 | ‖ O | $C_2H_5$ | H | S | 36.50 |
| 400 | \| $OCH_3$ cis/trans | H | H | O | 69.4 |

EXAMPLE 21

Preparation of (S)-N-(1,2,3,4-tetrahydro-1-naphthyl)acetamide (S)-1,2,3,4-tetrahydro-1-naphthylamine (26.9 g.) is dissolved in 200 ml. of toluene and 36 g. of acetic anhydride is added while the temperature from the reaction exotherm is moderated at 50° C. to 60° C. with an ice-bath. The solution is heated to reflux for 0.5 hr. and then stirred at room temperature overnight. The mixture is then evaporated to dryness and the residue is washed well with ether. On drying, 26.1 g. of the title compound, m.p. 153° C. to 155° C., is obtained.

EXAMPLE 22

Preparation of (S)-N-(1,2,3,4-tetrahydro-4-oxo-1-naphthyl)-acetamide

By the method described in Example 1, (S)-N-(1,2,-3,4-tetrahydro-1-naphthyl)acetamide is oxidized to afford (S)-N-(1,2,3,4-tetrahydro-7-oxo-1-naphthyl)acetamide, which is used directly as a crude material in preparing derivatives.

The crude title compound after ether washing melts at 141° C. to 157° C. dec.

EXAMPLE 23

Preparation of cis and trans-(S)-N-(1,2,3,4-tetrahydro-4-hydroxy-1-naphthyl-)acetamide By the method described in Example 9, (S)-N-(1,2,-3,4-tetrahydro-4-oxo-1-naphthyl)acetamide is reduced to afford a mixture of cis and trans title compound which is separable by chromotography.

EXAMPLE 24

Preparation of cis and trans-(S)-N-(1,2,3,4-tetrahydro-4-methoxy-1-naphthyl-)acetamide By the method described in Example 10, the mixture of cis and trans-(S)-N-(1,2,3,4-tetrahydro-4-tetrahydro-4-hydroxy-1-naphthyl)acetamide is methylated to afford the mixture of cis and trans (S)-N-(1,2,3,4-tetrahydro-4-methoxy-1-naphthyl)-acetamide.

EXAMPLE 25

Preparation of (S)-1,2,3,4-tetrahydro-4-oxo-1-naphthylamine hydrochloride

A 20 g. sample of (S)-N-(1,2,3,4-tetrahydro-4-oxo-1-naphthyl)acetamide is stirred with 600 ml. of 6N HCl and the mixture is heated to reflux for 24 hours. After allowing to stand for 48 hours, the aqueous solution is decanted and the remaining tar is washed with 200 ml. of $H_2O$. The combined aqueous solutions are washed with $CHCl_3$ (3×200 ml.) and the organic washes are counter-washed with 200 ml. of $H_2O$. The combined aqueous solutions are filtered through celite and the filter cake is washed with 50 ml. of $H_2O$. The aqueous filtrates are then evaporated to dryness in vacuo to afford the title compound, m.p. 230° C. to 235° C.

Conversion of this title compound to the biologically active urea is accomplished by dissolving 1 g. of the amine hydrochloride in 100 ml. of $H_2O$ and adding 8.9 g. of KOCN in 25 ml. of $H_2O$ to the solution. After stirring at room temperature for 18 hours, the (S)-1,2,3,4-tetrahydro-4-oxo-1-naphthylurea is collected, washed well with H₂O, and dried. This material melts at 228° C. to 230° C. dec. After recrystallization twice from MeOH, it melts at 240° C. to 242° C. dec.

EXAMPLE 26

The following compounds of structure B are prepared by reducing compounds of structure A by the method described in Example 4.

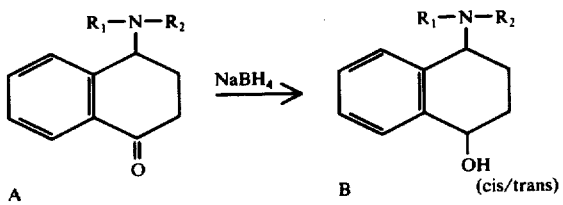

wherein R₁ is hydrogen; R₂ is defined as benzoyl, trichloro-

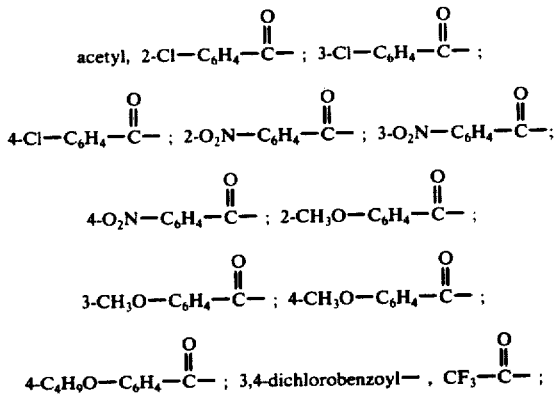

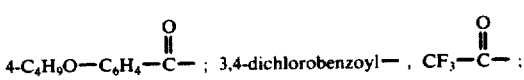

and when R₁ and R₂ are taken together with the associated nitrogen they are succinimido, maleimido and phthalimido.

EXAMPLE 27

The following compounds of structure D are prepared by methylating compounds of structure C by the method described in Example 10.

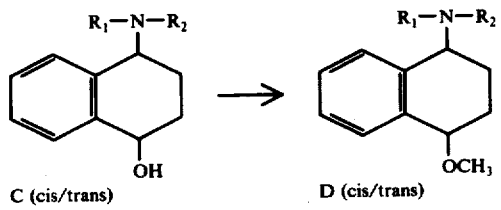

wherein R₁ is hydrogen; R₂ is defined as benzoyl, trichloroacetyl,

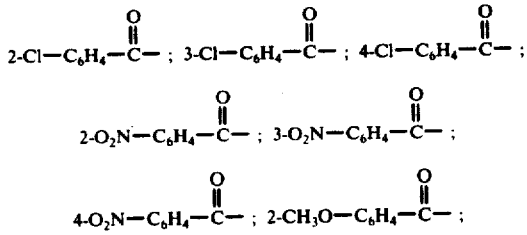

and when R₁ and R₂ are taken together with the associated nitrogen they are succinimido, maleimido and phthalimido.

EXAMPLE 28

Preparation of 1,2,3,4-Tetrahydro-4-hydroxy-1-naphthylamine

By the method described in Example 11, a mixture of cis and trans-N-(1,2,3,4-tetrahydro-4-hydroxy-1-naphthyl)-acetamide is hydrolyzed to afford the title compound.

Similarly, the corresponding trichloroacetamide, benzamide and phthalimide are hydrolyzed to afford the title compound.

EXAMPLE 29

Preparation of 1-Methyl-3-(1,2,3,4-tetrahydro-4-oxo-1naphthyl)urea

In the manner described in Example 19, 1,2,3,4-tetrahydro-4-oxo-1-naphthylamine is allowed to react with methyl isocyanate to afford the title compound, m.p. 220° C. to 223° C.

Similarly, 1,2,3,4-tetrahydro-4-hydroxy-1-naphthylamine is allowed to react with an equivalent amount of methyl isocyanate to afford 1-methyl-3-(1,2,3,4-tetrahydro-4-hydroxy-1-naphthyl)urea, m.p. 172° C. to 180° C.

I claim:

1. A compound of the formula:

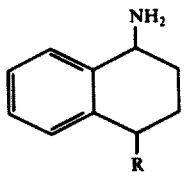

wherein R is oxo, hydroxy or alkoxy $C_1$–$C_4$; the racemic mixtures and the optical isomers thereof; the cis and trans isomers thereof when R is hydroxy or alkoxy $C_1$–$C_4$; and the halogen acid salts thereof.

2. The racemic mixture according to claim 1, 1,2,2,3-tetrahydro-4-oxo-1-naphthylamine.

3. The optical isomers according to claim 1, 1,2,3,4-tetrahydro-4-oxo-1naphthylamine.

4. The racemic mixture according to claim 1, 1,2,3,4-tetrahydro-4-methoxy-1-naphthylamine.

5. The optical isomers according to claim 2, 1,2,3,4-tetrahydro-4-methoxy-1-naphthylamine.

6. The racemic mixture according to claim 1, 1,2,3,4-tetrahydro-4-hydroxy-1-naphthylamine.

7. The cis and trans isomers according to claim 1, 1,2,3,4-tetrahydro-4-hydroxy-1-naphthylamine.